United States Patent
Suoninen et al.

(10) Patent No.: US 9,745,895 B2
(45) Date of Patent: Aug. 29, 2017

(54) METHOD AND AN APPARATUS FOR PRODUCING ENERGY BY RECYCLING MATERIALS DURING A FUEL COMBUSTION PROCESS

(75) Inventors: Esa Suoninen, Degerby (FI); Martti Surakka, Nukari (FI)

(73) Assignee: Fortum Oyj, Espoo (FI)

( * ) Notice: Subject to any disclaimer, the term of this patent is extended or adjusted under 35 U.S.C. 154(b) by 788 days.

(21) Appl. No.: 14/117,657

(22) PCT Filed: May 18, 2012

(86) PCT No.: PCT/FI2012/050473
§ 371 (c)(1),
(2), (4) Date: Jan. 8, 2014

(87) PCT Pub. No.: WO2012/156588
PCT Pub. Date: Nov. 22, 2012

(65) Prior Publication Data
US 2014/0338361 A1 Nov. 20, 2014

(30) Foreign Application Priority Data
May 18, 2011 (FI) ........................................ 20115478

(51) Int. Cl.
*F02C 7/00* (2006.01)
*F02C 6/10* (2006.01)
*C12M 1/00* (2006.01)
*C12M 1/107* (2006.01)
*F22B 1/18* (2006.01)
*F02C 3/28* (2006.01)

(52) U.S. Cl.
CPC .............. *F02C 6/10* (2013.01); *C12M 21/02* (2013.01); *C12M 21/04* (2013.01); *C12M 43/04* (2013.01); *F02C 3/28* (2013.01); *F22B 1/1807* (2013.01); *Y02E 20/363* (2013.01); *Y02E 50/343* (2013.01)

(58) Field of Classification Search
CPC .......... C12M 21/02; C12M 21/04; F02C 6/10; F02C 6/18; F02C 3/22; Y02E 20/16
See application file for complete search history.

(56) References Cited

U.S. PATENT DOCUMENTS

| | | |
|---|---|---|
| 2005/0064577 A1 | 3/2005 | Berzin |
| 2007/0012041 A1 | 1/2007 | Goldman |
| 2007/0048848 A1 | 3/2007 | Sears |
| 2008/0050800 A1* | 2/2008 | McKeeman ............ C11C 3/003 435/262.5 |

(Continued)

FOREIGN PATENT DOCUMENTS

| | | |
|---|---|---|
| DE | 10 2009 051 927 | 5/2011 |
| EP | 0 878 533 A2 | 11/1998 |

(Continued)

OTHER PUBLICATIONS

Swedish Office Action dated Aug. 7, 2015 (15 pages).

*Primary Examiner* — Derek Battisti
(74) *Attorney, Agent, or Firm* — Cozen O'Connor

(57) ABSTRACT

The present invention relates to a method for producing energy by recycling materials during a fuel combustion process, wherein the fuel combustion process comprises combusting fuel introduced into the fuel combustion process. Further, the invention relates to an apparatus for producing energy by recycling materials during a fuel combustion process.

13 Claims, 2 Drawing Sheets

(56) References Cited

U.S. PATENT DOCUMENTS

| | | | | |
|---|---|---|---|---|
| 2008/0250791 A1* | 10/2008 | Fromson | .................. | C01B 7/03 |
| | | | | 60/783 |
| 2009/0029446 A1 | 1/2009 | O'Rear | | |
| 2009/0229595 A1* | 9/2009 | Schwartz, Jr. | ........ | F28D 21/001 |
| | | | | 126/344 |
| 2009/0282882 A1* | 11/2009 | Verhave | .................... | C05F 3/00 |
| | | | | 71/7 |
| 2010/0105127 A1* | 4/2010 | Ginsburg | ................ | C02F 11/04 |
| | | | | 435/262 |
| 2010/0112242 A1* | 5/2010 | Medoff | .................... | C08H 8/00 |
| | | | | 428/22 |
| 2010/0150802 A1* | 6/2010 | Gilliam | ................. | B01D 53/62 |
| | | | | 423/220 |
| 2010/0151550 A1* | 6/2010 | Signes Nunez | ......... | C10L 1/023 |
| | | | | 435/165 |
| 2010/0297739 A1* | 11/2010 | Steiner | .................. | C12M 21/02 |
| | | | | 435/257.1 |

FOREIGN PATENT DOCUMENTS

| | | |
|---|---|---|
| WO | 2009/034365 | 3/2009 |
| WO | WO 2009/086307 | 7/2009 |
| WO | 2009/136280 | 11/2009 |

\* cited by examiner

METHOD AND AN APPARATUS FOR PRODUCING ENERGY BY RECYCLING MATERIALS DURING A FUEL COMBUSTION PROCESS

CROSS-REFERENCE TO PRIOR APPLICATIONS

This application is a U.S. national stage of international application PCT/FI2012/050473, filed on May 18, 2012, which claims priority from Finland Application No. 20115478, filed on May 18, 2011, all of which are herein incorporated by reference.

FIELD OF THE INVENTION

The present invention relates to a method for producing energy by recycling materials during a fuel combustion process. Further, the invention relates to an apparatus for producing energy by recycling materials during a fuel combustion process.

BACKGROUND OF THE INVENTION

Fuel combustion is a process by which a fuel is consumed in an exothermic chemical reaction that releases heat and light. Usually the fuel that is combusted is a hydrocarbon that reacts with the oxygen in the air. The main use of fuel combustion is energy. The most common fuels used for the production of energy are fossil fuels, which are made up of ancient, decomposed organic matter. Oil, coal, and natural gas are three of the most common fossil fuels used in fuel combustion reactions.

Drawback of the fuel combustion process is that the power plant sources, e.g. coal-based power plants, produce flue gas emissions during the fuel combustion process. The flue gas released into the air affect the environment.

Prior art recognizes the use of flue gas, comprising e.g. carbon dioxide and nitrogen dioxide, as nutrient for algae. US 2007/0048848 A1 discloses a process comprising directing carbon dioxide in flue gas exhaust from a coal fired power plant into an algae bioreactor and directing the oxygen produced from photosynthesis of the algae in the algae bioreactor into the power plant process for supporting efficient combustion.

However, the inventors have recognized the need of more efficiently recycling materials during the fuel combustion process for reducing the amount of especially fossil fuels needed to be used in the fuel combustion process.

PURPOSE OF THE INVENTION

A purpose of the invention is to provide a new type of method for producing energy by recycling materials during a fuel combustion process. Further, a purpose of the invention is to provide an apparatus for producing energy by recycling materials during a fuel combustion process.

SUMMARY OF THE INVENTION

The method according to the present invention is characterized by what is presented in claim 1.

The method according to the present invention for producing energy by recycling materials during a fuel combustion process taking place in a fuel combustion device, which is a boiler or a furnace, wherein the fuel combustion process comprises combusting fuel introduced into the fuel combustion process, comprises the following steps of:
  introducing a stream of flue gas comprising carbon dioxide and produced in the fuel combustion process into a biomass cultivating process, where the flue gas takes part in the production of biomass and oxygen;
  introducing at least part of the biomass produced in the biomass cultivating process into a biogas production process, where the biomass takes part in the production of biogas;
  introducing at least part of the oxygen produced in the biomass cultivating process into the fuel combustion process;
  introducing at least part of the biogas produced in the biogas production process into the fuel combustion process, where the biogas is combusted as fuel; and
  introducing combustion air into the fuel combustion process; such that the need to introduce fuel selected from a group consisting of fossil fuel comprising coal, biofuel, industrial waste, municipal waste and any combination thereof, into the fuel combustion process during the fuel combustion process in addition to the biogas produced in the biogas production process and introduced into the fuel combustion process is reduced.

The present invention relates to an apparatus for producing energy by recycling materials during a fuel combustion process, wherein the apparatus comprises a fuel combustion device, which is a boiler or a furnace, for combusting fuel introduced into the fuel combustion device, and wherein the apparatus further comprises:
  means for introducing a stream of flue gas comprising carbon dioxide and produced in the fuel combustion device into a biomass cultivating device;
  a biomass cultivating device for producing biomass and oxygen;
  means for introducing at least part of the biomass produced in the biomass cultivating device into a biogas reactor;
  a biogas reactor for producing biogas;
  means for introducing at least part of the oxygen produced in the biomass cultivating device into the fuel combustion device;
  means for introducing at least part of the biogas produced in the biogas reactor into the fuel combustion device for combusting biogas as fuel; and
  means for introducing combustion air into the fuel combustion device; and in that the apparatus is configured such that the need to introduce fuel selected from a group consisting of fossil fuel comprising coal, biofuel, industrial waste, municipal waste and any combination thereof, into the fuel combustion device during the fuel combustion process in addition to the biogas produced in the biogas reactor and introduced into the fuel combustion device is reduced.

The present invention, where materials are recycled during the fuel combustion process results in the advantage effect that a lesser amount of fuel, e.g. fossil fuel, is needed to be introduced into the fuel combustion process in addition to the biogas produced in the biogas production process and introduced into the fuel combustion process when compared to a fuel combustion process, where such recycling of materials is not performed for producing the same amount of energy.

According to one embodiment of the present invention the method comprises producing primary energy. According to one embodiment of the present invention the method comprises producing electric energy. According to one embodiment of the present invention the apparatus is configured to produce primary energy. According to one embodiment of the present invention the apparatus is configured to produce electric energy.

According to one embodiment of the present invention the method comprises recovering energy produced in the fuel combustion process. According to one embodiment of the present invention the apparatus comprises means for recovering energy produced in the fuel combustion device. The means for recovering energy produced in the fuel combustion device can comprise any suitable means to be used for recovering the energy.

In this specification, unless otherwise stated, the term "fuel combustion process" is used to address any process during which fuel is combusted in order to produce energy.

According to one embodiment of the present invention the fuel is selected from a group consisting of fossil fuel, biofuel, industrial by-product, industrial waste, municipal waste and any combination thereof. According to one embodiment of the present invention the fossil fuel is selected from a group consisting of coal, petroleum, natural gas and any combination thereof. According to one embodiment of the present invention the fossil fuel comprises coal. According to one embodiment of the present invention the biofuel comprises biogas and/or solid biofuel. Alga biomass, wood, sawdust, grass cutting and green waste can be mentioned as examples of solid biofuels. According to one embodiment of the present invention the fuel comprises biogas. According to one embodiment of the present invention the fuel comprises methane ($CH_4$). According to one embodiment of the present invention the fuel comprises a combination of fossil fuel and biogas.

The fuel combustion process takes place in a fuel combustion device, which is a boiler, or a furnace. The boiler or furnace is to be understood as a fuel combustion device, wherein solid, liquid, and/or gas form fuel can be combusted.

According to the present invention a stream of flue gas comprising carbon dioxide is introduced into the biomass cultivating process. According to the present invention the apparatus comprises means for introducing a stream of flue gas comprising carbon dioxide into a biomass cultivating device. According to one embodiment of the present invention the flue gas is spread into bubbles in the growing media of the biomass. The means for introducing a stream of flue gas into a biomass cultivating device can comprise any suitable means to be used for introducing a stream of flue gas into a biomass cultivating device.

According to one embodiment of the present invention the stream of flue gas further comprises NO, $NO_2$ and/or $N_2$. According to one embodiment of the present invention the flue gases are produced as a result of the fuel combustion process. According to one embodiment of the present invention the flue gases are processed in a suitable manner before they are introduced into the biomass cultivating process.

According to one embodiment of the present invention the biomass cultivating device comprises a photobioreactor (PBR) or a covered cultivation pond.

In this specification, unless otherwise stated, the term "biomass cultivating process" is used to address any process during which biomass and oxygen is formed as a result of photosynthesis of the biomass. The formula of photosynthesis is the following:

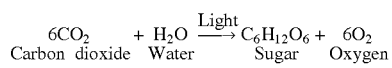

When biomass is cultivated it uses carbon dioxide as a feed for its photosynthesis. As a result of photosynthesis, the carbon is taken into the biomass and oxygen is released. Of each carbon dioxide molecule, one carbon is taken to the biomass and two atoms of oxygen are released.

The cultivated biomass can be collected by using suitable equipment. As an example only it can be mentioned that the solid matter content of biomass, e.g. algae, produced in the biomass cultivating process is between 0.05-0.5%, usually between 0.1-0.2%. For further use, the biomass can be thickened to a solid matter content between 1.5-3%, for example between 2-2.5%, by using a filter or a centrifuge.

According to one embodiment of the present invention the biomass is selected from a group consisting of algae, water grass and a combination thereof. According to one embodiment of the present invention the biomass comprises algae. The algae species of *Chlorella, Closterium* and *Spirulina*, as well as any combination thereof can be mentioned as examples to be used in the present invention. Also other algae species or combinations of different species can be used in the present invention.

At least part of the oxygen released from the photosynthesis at the biomass cultivating process can be used in the fuel combustion process. It was surprisingly noticed that the oxygen produced in the biomass cultivating process and directed into the fuel combustion process was able to replace at least part of the combustion air needed in the fuel combustion process. The advantage of replacing at least part of the combustion air with the oxygen from the biomass cultivating process in the fuel combustion process is that the problems relating to nitrogen in the air, as described below, are decreased.

The means for introducing at least part of the oxygen produced in the biomass cultivating device into the fuel combustion device can comprise any suitable means to be used for introducing the oxygen into the fuel combustion device.

At least part of the produced biomass is introduced into the biogas production process. In this specification, unless otherwise stated, the term "biogas production process" is used to address any process during which biogas is produced. Biogas is to be understood as a gas produced by the biological breakdown of organic matter in the absence of oxygen.

The means for introducing at least part of the biomass produced in the biomass cultivating device into the biogas reactor can comprise any suitable means to be used for introducing the biomass into the biogas reactor.

According to one embodiment of the present invention the solids content of the composition comprising biomass introduced into the biogas production process is below 3%, preferably below 2.5%, and more preferably between 1.5-2%.

According to one embodiment of the present invention the residence time in the biogas production process is at most 5 days, preferably at most 4 days, and more preferably from 1 to 2 days.

According to one embodiment of the present invention the biogas comprises methane, carbon dioxide or a combination comprising methane and carbon dioxide. According to one embodiment of the present invention the biogas comprises as its main components methane (50-75%) and carbon dioxide (49-24%). The biogas may further comprise a small amount, usually at most 1%, of other gases as examples of which hydrogen and hydrosulphates can be mentioned.

At least part of the biogas produced in the biogas production process is introduced into the fuel combustion process. According to one embodiment of the present invention at least part of the biogas produced in the biogas production process is introduced into the fuel combustion process by guiding the biogas into a gas distributing network. The gas distributing network, e.g. a pipeline, enables also the introduction of other gaseous fuel into the fuel combustion process simultaneously with the biogas fuel. Natural gas can be mentioned as an example of such gaseous fuel.

According to one embodiment of the present invention at least part of the biogas produced in the biogas production process is converted into a liquefied biogas (LBG) form before the step of introducing the biogas into the fuel combustion process. The term "liquefied biogas" is used to address the biogas produced in the biogas production process, i.e. in the biogas reactor, that has been converted temporarily to a liquid form. The liquid form of the biogas makes the transport and storage of the biogas easier. The liquefied biogas is, however, regasified before being directed or introduced into the fuel combustion process.

The biogas introduced into the fuel combustion process is used as fuel. As an example only it can be mentioned that when using methane as fuel in a coal-fired boiler up to 50%, preferably up to 80%, of the coal needed may be replaced by the methane. The advantage of recycling methane from the biogas production process into the fuel combustion process is thus that the use of especially fossil fuel in markedly decreased.

The means for introducing at least part of the biogas produced in the biogas reactor into the fuel combustion device can comprise any suitable means to be used for introducing the biogas into the fuel combustion device. The means for introducing at least part of the biogas produced in the biogas reactor into the fuel combustion device can comprise e.g. a gas distributing network via which the biogas is guided into the fuel combustion device.

According to one embodiment of the present invention the biomass is collected and thickened before it is introduced into the biogas production process.

According to one embodiment of the present invention 300-1500 kg, preferably 650-850 kg, and more preferably 740-800 kg of oxygen produced in the biomass cultivating process is introduced into the fuel combustion process per 1000 kg of carbon dioxide produced in the fuel combustion process.

According to one embodiment of the present invention 100-800 kg, preferably 300-400 kg, and more preferably 330-370 kg of biogas produced in the biogas production process is introduced into the fuel combustion process per 1000 kg of carbon dioxide produced in the fuel combustion process.

According to one embodiment of the present invention 200-900 kg, preferably 400-600 kg, and more preferably 450-550 kg of biomass is produced in the biomass cultivating process per 1000 kg of carbon dioxide introduced into the biomass cultivating process.

According to one embodiment of the present invention 0-500 kg, preferably 0-100 kg, and more preferably 40-80 kg of fuel is introduced into the fuel combustion process in addition to the biogas produced in the biogas production process and introduced into the fuel combustion process per 1000 kg of carbon dioxide produced in the fuel combustion process.

According to one embodiment of the present invention 1000-2000 kg, preferably 1200-1800 kg, and more preferably 1550-1600 kg of combustion air is introduced into the fuel combustion process per 1000 kg of carbon dioxide produced in the fuel combustion process.

According to one embodiment of the present invention 100-500 kg, preferably 250-450, and more preferably 340-400 kg of water is recovered from the fuel combustion process per 1000 kg of carbon dioxide produced in the fuel combustion process.

According to one embodiment of the present invention 800-1600 kg, preferably 950-1450 kg, and more preferably 1150-1350 kg of nitrogen gas is produced in the fuel combustion process per 1000 kg of carbon dioxide produced in the fuel combustion process.

According to one embodiment of the present invention the method comprises introducing at least part of fermentation sludge formed in the biogas production process into the biomass cultivating process. The fermentation sludge can serve as nutrient for e.g. the algae. According to one embodiment of the present invention the apparatus comprises means for introducing at least part of fermentation sludge formed in the biogas reactor into the biomass cultivating device. The means for introducing at least part of fermentation sludge formed in the biogas reactor into the biomass cultivating device can comprise any suitable means to be used for introducing the fermentation sludge into the biomass cultivating device. At least part of fermentation sludge formed in the biogas reactor can be introduced into the biomass cultivating device by using a pump.

According to one embodiment of the present invention the method comprises introducing growing media comprising waste water into the biomass cultivating process. According to one embodiment of the present invention the apparatus comprises means for introducing growing media comprising waste water into the biomass cultivating device. In order to produce biomass in addition to carbon dioxide also other nutrients comprising e.g. nitrogen, phosphorous and micronutrients can be introduced into the biomass cultivating process. At least part of the nitrogen can be introduced with the flue gas and according to one embodiment of the present invention waste water is used as growing media. The advantage of using waste water in the method according to the present invention is that when biomass collects the nutrients needed for its growing, the wastewater is simultaneously being cleaned.

The combustion products of methane are carbon dioxide and water. Since the water produced requires almost half of the oxygen introduced from the biomass cultivating process, additional oxygen is introduced into the fuel combustion process in accordance with one embodiment of the present invention. The additional oxygen is needed to replace oxygen lost in form of water.

Thus, according to the present invention the method comprises introducing combustion air into the fuel combustion process. According to the present invention the apparatus comprises means for introducing combustion air into the fuel combustion device. Said means can comprise any suitable means for introducing combustion air into the fuel combustion device. According to one embodiment of the present invention the combustion air comprises oxygen, nitrogen or a combination comprising oxygen and nitrogen.

According to one embodiment of the present invention the fuel introduced into the fuel combustion process comprises fossil fuel. According to one embodiment of the present invention the fuel introduced into the fuel combustion process comprises coal. According to one embodiment of the present invention the apparatus comprises means for introducing fuel into the fuel combustion device. The means for introducing fuel into the fuel combustion device can comprise any suitable means to be used for introducing the fuel into the fuel combustion device.

According to one embodiment of the present invention the method comprises recovering water from the fuel combustion process. According to one embodiment of the present invention the apparatus comprises means for recovering water from the fuel combustion device. The means for recovering water from the fuel combustion device can comprise any suitable means to be used for recovering water from the fuel combustion device.

According to one embodiment of the present invention the method comprises introducing carbon dioxide into the biomass cultivating process in addition to the carbon dioxide contained in the stream of flue gas. According to one embodiment of the present invention the apparatus comprises means for introducing carbon dioxide into the biomass cultivating device in addition to the carbon dioxide introduced by the means for introducing a stream of flue gas comprising carbon dioxide and produced in the fuel combustion device into a biomass cultivating device. Said means can comprise any suitable means for introducing said additional carbon dioxide into the biomass cultivating device.

According to one embodiment of the present invention the method comprises introducing at least part of the biomass produced in the biomass cultivating process into the fuel combustion process, where the biomass is combusted as fuel. According to one embodiment of the present invention the apparatus comprises means for introducing at least part of the biomass produced in the biomass cultivating device into the fuel combustion device. The means for introducing at least part of the biomass produced in the biomass cultivating device into the fuel combustion device can comprise any suitable means for introducing the biomass into the fuel combustion device.

According to one embodiment of the present invention the method comprises preventing nitrogen from accumulating during the method. According to one embodiment of the present invention the apparatus comprises means for removing nitrogen.

According to one embodiment of the present invention the method can be realized as a continuous circulation of the materials to be recycled. As a result of continuously circulating the materials to be recycled in accordance with the present invention there is continuously produced energy in the fuel combustion unit until the process is stopped.

According to one embodiment of the present invention the method comprises one or more further processing steps. As examples only, the one or more further processing steps may comprise processing the flue gas in a suitable manner before it is introduced into the biomass cultivating process, processing the biomass in a suitable manner before it is introduced into the biogas production process, processing the biogas in a suitable manner before it is introduced into the fuel combustion process, processing the oxygen in a suitable manner before it is introduced into the fuel combustion process, etc. In a similar manner, according to one embodiment of the present invention also the apparatus comprises one or more further devices and/or means.

The embodiments of the invention described hereinbefore may be used in any combination with each other. Several of the embodiments may be combined together to form a further embodiment of the invention. A method or an apparatus, to which the invention is related, may comprise at least one of the embodiments of the invention described hereinbefore.

An advantage of the present invention is that the amount of the non-renewable resources of fossil fuels, e.g. coal, to be used in the fuel combustion process can be markedly decreased when recycling the materials in accordance with the present invention. Recycling the biogas comprising methane produced in the biogas production process to be used as fuel in the fuel combustion process decreases the amount of fuel needed to be introduced from an outside source into the fuel combustion process. As an example only, it can be mentioned that in traditional fuel boilers, where the fuel combustion process takes place, about 350 kg of coal is needed to be introduced into the boiler per 1000 kg of carbon dioxide produced. When the loop is closed, i.e. the biogas is directed into the fuel boiler, it can constitute about 80% of the fuel needed. Thus only about 60 kg of coal from an outside source is needed per 1000 kg of carbon dioxide produced.

An advantage of the method according to the present invention is that by capturing oxygen produced in the biomass cultivation process and by directing the captured oxygen into the boiler of a combustion process, the need for additional combustion air to be used in the combustion process is remarkably reduced. Up to about 60% of the combustion air needed in the fuel combustion process can be replaced by the oxygen introduced from the biomass cultivating process. The main components of atmosphere are oxygen (about 21%) and nitrogen (about 78%). As nitrogen is an inert gas the amount of nitrogen introduced into the boiler in the combustion air has to be taken into account when dimensioning the device. The use of air introduced into the boiler usually leads to a situation where e.g. tubes and chambers are over-dimensioned. As the present invention leads to a lesser amount of combustion air introduced into the boiler also the costs of the device are markedly reduced. Further, removing the nitrogen from air requires massive investments, which are thus not needed when using the method and apparatus in accordance with the present invention.

An advantage of the present invention is the possibility of a smaller oxygen factory in connection with the boiler usually used in the oxygen combustion technology.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION OF THE INVENTION

Reference will now be made in detail to the embodiments of the present invention, examples of which are illustrated in the accompanying drawings.

The description below discloses some embodiments of the invention in such a detail that a person skilled in the art is able to utilize the invention based on the disclosure. Not all steps of the embodiments are discussed in detail, as many of the steps will be obvious for the person skilled in the art based on this specification.

For reasons of simplicity, item numbers will be maintained in the following exemplary embodiments in the case of repeating components.

Figure 1:
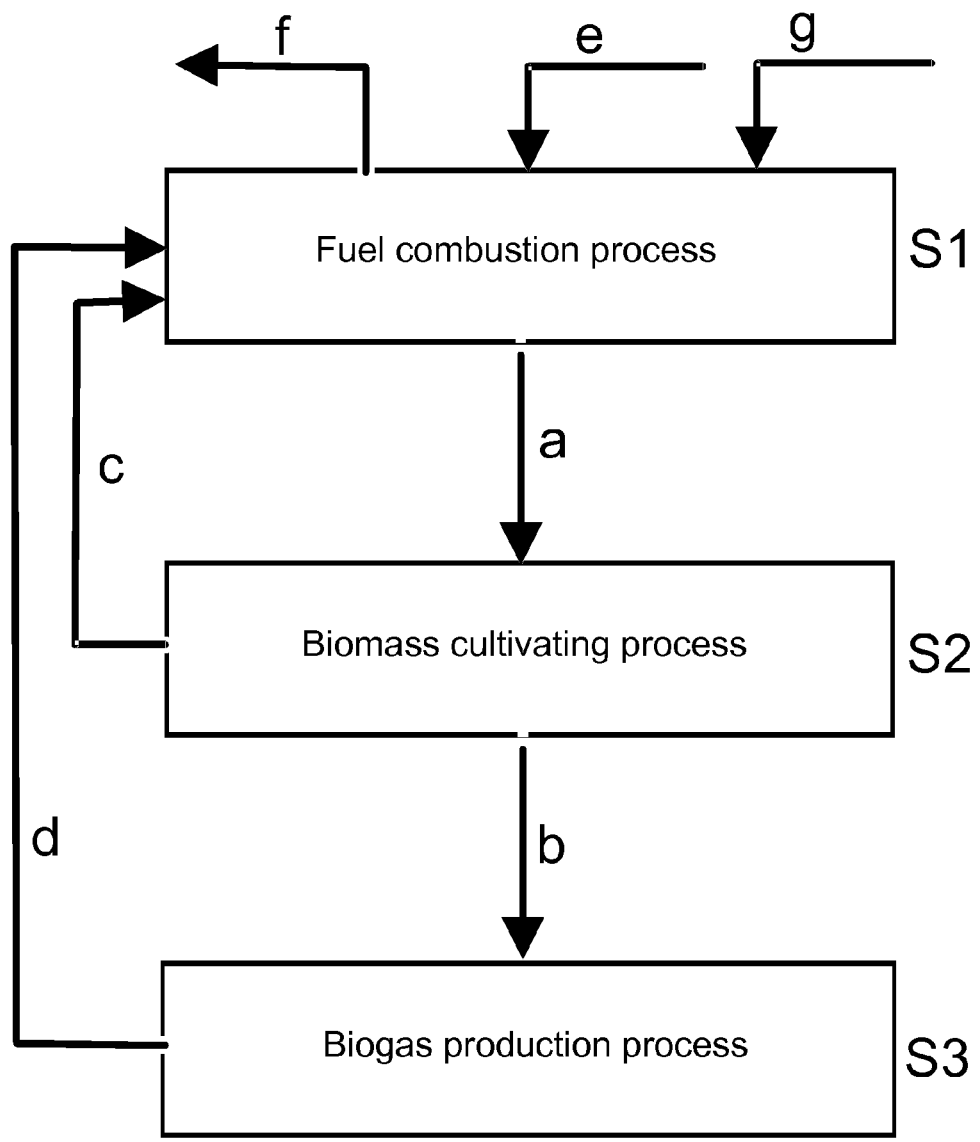
FIG. 1 is a flowchart illustrating one embodiment of a method according to the present invention.

In step S1 of an embodiment of the method according to FIG. 1, there is produced energy as presented in step f in a fuel combustion process, taking place in a fuel combustion device, which is a boiler or a furnace, of step S1 by burning fuel, e.g. fossil fuel such as coal. As a result of the combustion process flue gas comprising carbon dioxide is produced. The stream of flue gas is introduced in step a into a biomass cultivating process, where the flue gas takes part in the photosynthesis of biomass, e.g. algae.

As a result of the biomass cultivating process in step S2 biomass is produced, at least part of which is introduced in step b in FIG. 1 into step S3 comprising a biogas production process. Further, as a result of the biomass cultivating process in step S2 oxygen is produced, at least part of which is introduced into the fuel combustion process as presented in step c in FIG. 1.

The biomass introduced into the biogas production process is used for producing biogas in step S3. At least part of the biogas produced in step S3 is introduced into step S1 comprising the fuel combustion process as presented in step d in FIG. 1.

As a result of the recycling of materials presented in FIG. 1, the amount of fossil fuel needed to be introduced in step e into the fuel combustion process for producing energy in an efficient manner is decreased. Also the amount of combustion air to be introduced in step g into the fuel combustion process is decreased.

Obviously the method according to the present invention may comprise further steps, which will be obvious for the skilled person based on what is presented in this patent application.

Figure 2:
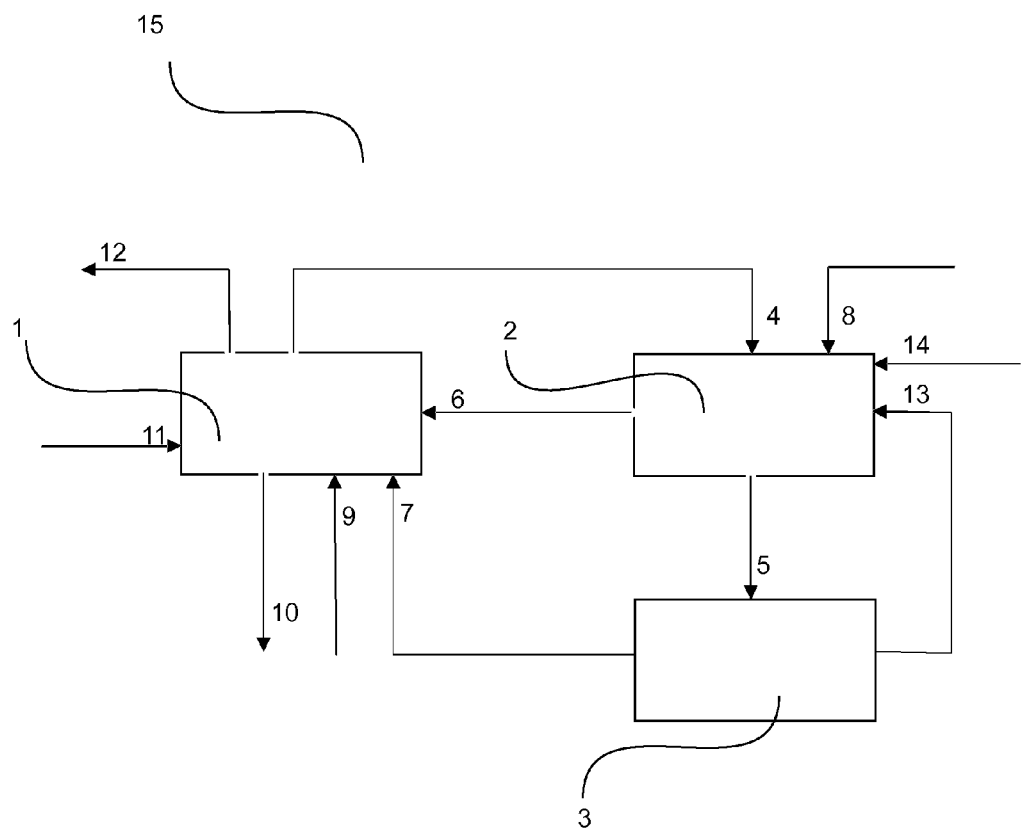
FIG. 2 is a schematical illustration of one embodiment of the apparatus according to the present invention.

The method according to the present invention can be realized by means of an apparatus illustrated schematically by the block diagram in FIG. 2. The apparatus 15 of FIG. 2 comprises a fuel combustion device 1, e.g. a boiler, by which fuel, e.g. fossil fuel such as coal, is combusted for producing energy at a power plant. The apparatus 15 of FIG. 2 further comprises means 4 for introducing or directing a stream of flue gas produced by a fuel combustion process at the fuel combustion device 1 into a biomass cultivating device 2, where the production of biomass and oxygen takes place.

At least part of the biomass produced at the biomass cultivating device is directed into a biogas reactor 3 by means 5 for introducing biomass into a biogas reactor 3. The biomass introduced into the biogas reactor 3 takes part in the production of biogas.

At least part of the biogas produced in the biogas reactor is introduced into the fuel combustion device 1 by means 7 for introducing biogas into the fuel combustion device.

The apparatus 15 presented in FIG. 2 further comprises means 13 for introducing at least part of the fermentation sludge produced in the biogas reactor 3 into the biomass cultivating device 2.

The biomass cultivating device 2 is further connected to means 14 for introducing carbon dioxide in addition to the carbon dioxide directed from the fuel combustion device into the biomass cultivating device and means 8 for introducing e.g. waste water into the biomass cultivating device 2.

In FIG. 2 is also illustrated means 6 for introducing at least part of the oxygen produced in the biomass cultivating device 2 into the fuel combustion device 1.

The apparatus of FIG. 2 further comprises means 9 for introducing combustion air into the fuel combustion device, means 11 for introducing fuel into the fuel combustion device, means 10 for recovering water from the fuel combustion device and means 12 for recovering the energy produced in the fuel combustion device.

Example 1

By applying the method in accordance with the present invention, there was manufactured, with an apparatus in accordance with the present invention, energy, i.e. primary energy, in a fuel combustion process by burning coal as fossil fuel in a boiler. The flue gases produced during the combustion process were recovered and introduced into a photobioreactor, where they took part in the growing of algae and the production of oxygen based on the photosynthesis of the algae. The photobioreactor used in this example was a glass tube reactor having a tube diameter of about 100 mm, a tube length of about 900 m and a reactor volume of about 30 m$^3$.

The algae used in this example were of *Closterium* species. Further, nutrients needed for the growth of algae was received e.g. from municipal waste water, which was used as growing media for the algae. As the algae grew it collected the nutrients from the waste water and thus simultaneously the waste water was cleaned. Further, the algae absorbed carbon dioxide and nitrogen while growing and simultaneously produced oxygen. Of each carbon dioxide molecule, one carbon was taken to the biomass, i.e. the algae growing, and two atoms of oxygen were released.

The oxygen produced by the algae in the biomass cultivating process was introduced into the boiler while at least part of the algae produced was introduced into a biogas reactor. The algae produced in the photobioreactor were centrifuged prior to being introduced into the biogas reactor such that the solids content increased from about 0.2% to about 1.5-2%.

The biogas reactor type used in this example was Upflow Anaerobic Sludge Blanker (UASB), which is a device designed to treat liquids having a very low content of solid matter. The retention time was 1-2 days, which allowed the treatment of large quantities of liquid or sludge with reasonably sized reactor. The reactor volume was in this example about 5 m$^3$.

Part of the fermentation sludge formed in the biogas reactor was returned by pumping it into the photobioreactor and the biogas, including methane and carbon dioxide, formed was introduced into the boiler. The biogas introduced into the boiler was used as fuel for the coal-fired boiler thus replacing at least 50% of the coal needed if the recycling of materials in accordance with the present invention would not have been performed.

As the combustion products of methane were carbon dioxide and water and as the water produced required almost half of the oxygen produced in the photobioreactor and introduced therefrom to the boiler, additional amount of oxygen was needed to replace the oxygen lost in form of water. Therefore, an additional amount of oxygen was introduced into the boiler in order to ensure an efficient combustion process.

Nitrogen accumulation was prevented during the process by using a suitable nitrogen removal device.

In a traditional coal-fired power plant about 350 kg of coal is needed for producing about 2.8 MWh (1.1 Mwh$_e$) of energy and simultaneously about 1000 kg of carbon dioxide. In this example in accordance with the present invention, where materials were recycled during the production of energy only about 60 kg of coal was needed to be introduced into the boiler in addition to the recycled materials for producing the same amount of energy. In the similar manner 1000 kg of carbon dioxide was produced. The introduction of 1000 kg of carbon dioxide and 1250 kg of $N_2$ into the photobioreactor produced about 770 kg of $O_2$, which was recycled into the boiler, and about 500 kg of algae, which were introduced into the biogas reactor. From the 500 kg of algae about 230 kg of methane and about 120 kg of carbon dioxide were formed in the biogas production process and introduced into the boiler. About 330 kg of additional oxygen and about 1250 kg of nitrogen gas, per 1000 kg of carbon dioxide produced in the fuel combustion device, were also introduced into the boiler. The fuel combustion process of example 1 resulted in recovering about 370 kg of water from the boiler per 1000 kg of carbon dioxide produced in the fuel combustion device.

Example 2

By applying the method in accordance with the present invention, there was manufactured, with an apparatus in accordance with the present invention, energy, i.e. primary energy, in a fuel combustion process by burning fuel in a boiler. The flue gas comprising carbon dioxide and nitrogen produced during the combustion process were recovered and introduced into a photobioreactor, where they took part in the growing of algae and the production of oxygen based on the photosynthesis of the algae. The photobioreactor used in this example was a glass tube reactor having a tube diameter of about 100 mm, a tube length of about 900 m and a reactor volume of about 30 $m^3$. Further, in addition to the carbon dioxide introduced into the photobioreactor with the stream of flue gas, additional carbon dioxide was introduced into the photobioreactor.

The algae used in this example were of *Spirulina* species. Further, nutrients needed for the growth of algae were received e.g. from municipal waste water, which was used as growing media for the algae. Further, the algae absorbed carbon dioxide and nitrogen while growing and simultaneously produced oxygen.

The oxygen produced by the algae in the photobioreactor was introduced into the boiler while at least part of the algae produced was introduced into a biogas reactor. However, the algae produced in the photobioreactor were centrifuged prior to being introduced into the biogas reactor such that the solids content increased from about 0.2% to about 1.5-2%.

The biogas reactor type used in this example was Upflow Anaerobic Sludge Blanker (UASB). The retention time was 1-2 days and the reactor volume was in this example about 5 $m^3$.

Part of the fermentation sludge formed in the biogas reactor was returned by pumping it into the photobioreactor and the biogas, including methane and carbon dioxide, formed was introduced into the boiler. The biogas introduced into the boiler was used as a fuel for fuel combustion process.

In a traditional coal-fired power plant about 350 kg of coal is needed for producing about 2.8 MWh (1.1 $Mwh_e$) of energy. Simultaneously about 1000 kg of carbon dioxide is formed. In this example the introduction of 1000 kg of carbon dioxide and 1250 kg of $N_2$ with the flue gas and of 430 kg of additional carbon dioxide into the photobioreactor produced about 1100 kg of $O_2$, which was recycled into the boiler, and about 770 kg of algae, which were introduced into the biogas reactor. From the 770 kg of algae about 354 kg of methane and about 185 kg of carbon dioxide were formed in the biogas production process and introduced into the boiler, where the biogas was used as fuel for the combustion process.

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A method for producing energy by recycling materials during a fuel combustion process (1) taking place in a fuel combustion device, which is a boiler or a furnace, wherein the fuel combustion process comprises combusting fuel introduced into the fuel combustion process, wherein the method comprises:
   introducing a stream of flue gas (4) comprising carbon dioxide and produced in the fuel combustion process (1) into a biomass cultivating process (2), where the flue gas takes part in the production of biomass and oxygen;
   introducing at least part of the biomass produced in the biomass cultivating process (2) into a biogas production process (3), where the biomass takes part in the production of biogas;
   introducing at least part of the oxygen produced in the biomass cultivating process (2) into the fuel combustion process (1);
   introducing at least part of the biogas produced in the biogas production process (3) into the fuel combustion process (1), where the biogas is combusted as fuel; and
   introducing combustion air (9) comprising oxygen and nitrogen into the fuel combustion process; such that the need to introduce fuel (11) selected from a group of fossil fuel comprising coal, biofuel, industrial waste, municipal waste and any combination thereof, into the fuel combustion process (1) during the fuel combustion process in addition to the biogas produced in the biogas production process (3) and introduced into the fuel combustion process is reduced.

2. The method of claim 1, wherein 300-1500 kg, preferably 650-850 kg, and more preferably 740-800 kg of oxygen (6) produced in the biomass cultivating process (2) is introduced into the fuel combustion process (I) per 1000 kg of carbon dioxide produced in the fuel combustion process.

3. The method of claim 1, wherein 100-800 kg, preferably 300-400 kg, and more preferably 330-370 kg of biogas (7) produced in the biogas production process (3) is introduced into the fuel combustion process (1) per 1000 kg of carbon dioxide produced in the fuel combustion process.

4. The method of claim 1, wherein 200-900 kg, preferably 400-600 kg, and more preferably 450-550 kg of biomass is produced in the biomass cultivating process (2) per 1000 kg of carbon dioxide (4) introduced into the biomass cultivating process.

5. The method of claim 1, wherein 0-500 kg, preferably 0-100 kg, and more preferably 40-80 kg of fuel (11) is introduced into the fuel combustion process (1) in addition to the biogas produced in the biogas production process (3) and introduced into the fuel combustion process per 1000 kg of carbon dioxide produced in the fuel combustion process.

6. The method of claim 1, wherein the stream of flue gas (4) further comprises NO, $NO_2$ and/or $N_2$.

7. The method of claim 1, wherein the biogas (7) comprises methane, carbon dioxide or a combination comprising methane and carbon dioxide.

8. The method of claim 1, wherein the biomass (5) is selected from a group of algae, water grass and a combination thereof.

9. The method of claim 1, wherein the method comprises introducing at least part of fermentation sludge (13) formed in the biogas production process (3) into the biomass cultivating process (2).

10. The method of claim 1, wherein the method comprises introducing growing media (8) comprising waste water into the biomass cultivating process (2).

11. The method of claim 1, wherein the fuel introduced into the fuel combustion process comprises coal.

12. The method of claim 1, wherein the method comprises recovering water (10) from the fuel combustion process (1).

13. The method of claim 1, wherein the method comprises introducing carbon dioxide (14) into the biomass cultivating process (2) in addition to the carbon dioxide contained in the stream of flue gas (4).

* * * * *